United States Patent [19]

Schoenwald et al.

[11] Patent Number: 4,820,737

[45] Date of Patent: Apr. 11, 1989

[54] LACRIMAL SECRETION STIMULANT (LSS)

[75] Inventors: Ronald D. Schoenwald; Charles F. Barfknecht, both of Iowa City, Iowa

[73] Assignee: University of Iowa Research Foundation, Iowa City, Iowa

[21] Appl. No.: 168,680

[22] Filed: Mar. 16, 1988

Related U.S. Application Data

[63] Continuation of Ser. No. 015,117, Feb. 17, 1987, abandoned.

[51] Int. Cl.$^4$ .............................................. A61K 31/14
[52] U.S. Cl. ................... 514/654; 514/643; 514/649; 514/651; 514/655; 514/912; 514/915
[58] Field of Search .............. 564/282, 284, 285, 287, 564/374; 514/643, 654, 912, 915, 649, 651, 638

[56] References Cited

U.S. PATENT DOCUMENTS 4,409,205  10/1983  Shively ................................ 514/912

OTHER PUBLICATIONS

Bumgardner et al., *J. Org. Chem.* vol. 44, No. 14, 1979, pp. 2348–2353.

*Primary Examiner*—Bruce D. Gray
*Attorney, Agent, or Firm*—Zarley, McKee, Thomte, Voorhees & Sease

[57]  ABSTRACT

Ophthalmic compositions useful as tear stimulants when topically applied to the eye for effective treatment of dry eye syndrome.

12 Claims, 1 Drawing Sheet

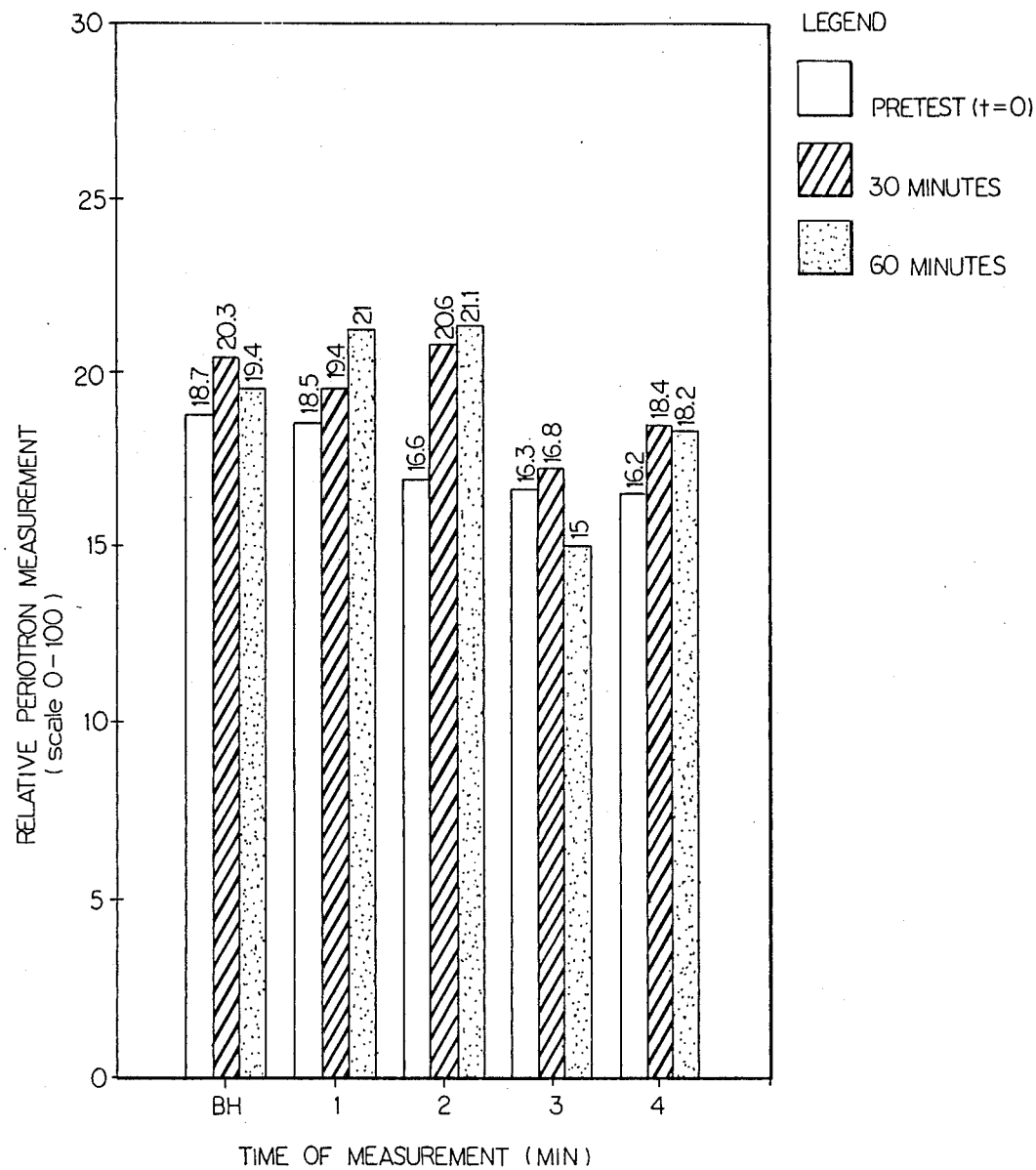

LACRIMAL SECRETION STIMULANT (LSS)

This is a continuation of copending application Ser. No. 015,117 filed on Feb. 17, 1987, now abandoned.

BACKGROUND OF THE INVENTION

Tear film disturbances account for eye symptoms in millions of Americans. At the present time, treatment primarily consists of replacing a defective tear film with artificial tear substitutes which are sold over-the-counter. The major limitation of these products is their short retention time in the eye. Patients must apply drops as often as every hour to obtain comfort from these products. Recent accomplishments have focused on developing aqueous solutions containing components which will stabilize the tear film or replace specific deficiencies.

A normal tear film is the product of: (1) aqueous secretion by the lacrimal gland and accessory lacrimal glands; (2) secretion of mucous primarily by the goblet cells of the conjunctiva; and, (3) lipids secreted by the meibomian gland and the glands of Zeis and Moll in the lids. Mucin, the innermost layer (0.035 $\mu$m), wets the lipophilic epithelial surface of the cornea with the middle aqueous layer. The aqueous layer (7 $\mu$m) contains dissolved proteins, carbohydrates, glycoproteins, oxygen, and inorganic salts. The outer lipid layer (0.1 $\mu$m) retards evaporation of the aqueous component.

Dry eye syndrome or keratoconjuctivitis sicca (KCS) can occur secondarily to many autoimmune diseases, and as a result of abnormalities in the precorneal tear film physiology. Besides an awareness of a chronically irritable sore eye by the patient, clinicians can diagnose dry eye syndrome by various measurements. These include a tear breakup time of 10 seconds or less in the absence of blinking, or a Schirmer test value of 5 mm or less. The latter involves leaving a standard strip of filter paper under the lower lid for 5 minutes. Other measurements are also helpful and include an observation of a smaller than normal marginal tear strip upon slitlamp examination, and/or a positive rose bengal stain which detects the presence of precipitated mucin and devitalized cells.

The stimulation of aqueous tears by a drug acting on the autonomic nervous system is an approach that had in the past limited success via a systemic route and little success via a topical route of administration. For example, some ophthalmologists have recommended oral ingestion of very dilute solutions of the cholinergic, pilocarpine, to stimulate tear secretion. However, unpleasant side effects have discouraged widespread use of ingested pilocarpine.

The stimulation of aqueous tears by the systemic or oral route has the undesirable side effect of causing systemic drug reactions by materials such as pilocarpine and other cholinergics. Moreover, by the time the active drug transfers itself through the body to the eye, its effect is significantly diluted. To date, there is no known effective composition for topical route of administration to treat dry eye syndrome.

As earlier indicated, the treatment with tear replacement compositions is not totally satisfactory because of their short retention time in the eye. Often the use by sufferers of dry eye syndrome of tear replacement products must continually apply drops even as often as every hour to obtain eye comfort. Moreover, especially for wearers of contact lenses, this problem of short time retention becomes quite real, rendering tear replacement unsatisfactory. In short, sufferers of dry eye syndrome are currently, for all practical purposes, excluded from the possibility of wearing contact lenses, since those lenses and their effective use, to say nothing of their comfortable use, necessarily depends upon adequate tear production.

It can be seen therefore that there is a very real and continuing need for an effective tear stimulant composition which can be administered topically. This invention has as its primary objective the fulfillment of this need.

Another objective of the present invention is to synthesize a series of compounds which have the utility of functioning effectively as tear, or in other words lacrimal, stimulants.

A still further objective of the present invention is to provide ophthalmic compositions which can function effectively as tear stimulants when topically administered to the eye.

A yet further objective of the present invention is to provide topical compositions which are not only effective tear stimulants but which also are non-toxic to the eye, and safe and effective, and as well cause little or no side effects.

An even further objective of the present invention is to provide topical ophthalmic compositions which stimulate tear production within the eye, thus eliminating the need for continual application of drops on a regular and frequent basis, such as is now required with currently sold tear replacement products.

Still another objective of the present invention is to provide a method of treatment of dry eye syndrome to stimulate the eye itself to produce more tears in a safe and efficacious manner.

Yet another objective of the present invention is to provide a method of inducing tear stimulation by topical administration of an ophthalmically active tear stimulant. The method of accomplishing these as well as other objectives of the invention will become apparent from the detailed description which follows hereinafter.

SUMMARY OF THE INVENTION

Tear stimulant compositions which can be topically administered to the eye for treatment of dry eye syndrome are provided. The compositions contain topically ophthalmically active compounds such as the preferred N-cyclohexyl-N-methyl-2-phenylethylamine and biologically acceptable salt forms thereof. This preferred compound, as well as others falling within the class below described, when placed in an ophthalmically acceptable pharmaceutical carrier and topically applied to the eye, stimulate the eye's own tear production. As a result, dry eye syndrome can be effectively treated. Because the treatment involves stimulation of tear production by the eye itself, as opposed to tear replacement, there is not a continuing need for eye drop addition on a nearly hourly basis, as there is with current tear replacement compositions.

BRIEF DESCRIPTION OF THE DRAWING

The FIGURE is a drawing showing treatment of the normal rabbit eye with some of the active compounds of the present invention and with a certain prior art compound bromhexine hydrochloride, which has been reported in published literature, especially German literature as having some effective use as a tear stimulant, see Prause, *Acta Ophthalmologica* 62, (1984) 489–497, entitled "Lacrimal And Salivery Secretion In Sjogrens Syndrome: The Effect of Systemic Treatment With Bromhexine" and U.S. Pat. No. 4,436,091, issued Mar. 20, 1984 to Gruber et al.

DETAILED DESCRIPTION OF THE INVENTION

In its broadest sense, this invention provides certain compounds that are believed new and most certainly have never been appreciated before for their utility as ophthalmically effective tear stimulants when topically applied to the eye. Compounds useful for this invention have the general formula:

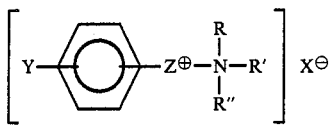

wherein Y is selected from the group consisting of hydrogen, hydroxy, amino, $C_1$ to $C_5$ alkyl, $C_1$ to $C_5$ hydroxyalkoxy and $C_1$ to $C_5$ alkoxy; Z is selected from the group consisting of $C_1$ to $C_6$ alkylene, $C_1$ to $C_6$ oxyalkylene, and $C_1$ to $C_6$ aminoalkylene; R is selected from the group consisting of $C_1$ to $C_6$ alkyl and $C_3$ to $C_7$ cycloalkyl; R' is selected from the group consisting of hydrogen, $C_1$ to $C_6$ alkyl and $C_3$ to $C_7$ cycloalkyl; R" is selected from the group of hydrogen and $C_1$ to $C_6$ alkyl; and X is a pharmaceutically acceptable counteranion.

Y can be in either an ortho-, meta- or para- position and is preferably hydrogen. Z likewise represents a moiety which can be ortho-, meta- or para- with respect to the Y, but is preferably para-positioned with respect to Y, and is preferably a $C_1$ to $C_6$ alkylene, and most preferably $C_2$ to $C_4$ alkyl. R is preferably a $C_1$ to $C_3$ alkyl, and most preferably methyl. R' is preferably cycloalkyl, most preferably cyclohexyl. R" is preferably hydrogen or $C_1$ to $C_3$ alkyl. X, as earlier mentioned, represents any pharmaceutically acceptable counteranion and is preferably a halogen, and most preferably chloride or bromide.

It can be seen that the compound as represented in the formula shown above is a quaternary ammonium ion salt form. If R" is hydrogen, the compound represents a tertiary amine salt. Other biologically acceptable salt forms of the compounds represented by the general formula above may of course be employed and are contemplated for use in this invention, as long as they have the necessary organic structure to provide the ophthalmically active tear stimulant when topically administered, and are still in a form which is pharmaceutically acceptable for topical administration, i.e. generally soluble in acceptable pharmaceutical carriers. The presently best known active compound for use in the ophthalmic compositions of the present invention is N-cyclohexyl-N-methyl-2-phenylethylamine of the formula:

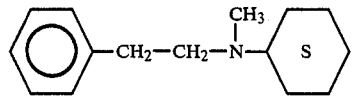

The ophthalmically effective tear stimulant compositions containing the above described active compounds will generally contain a small but tear stimulating effective amount of the active in an ophthalmically acceptable carrier. On a weight/volume basis it has been found that the amount of active may generally be within the range of about 0.1% to about 5%, and preferably from 0.2% to about 0.6% by weight/volume basis. The amounts of the active compound within these ranges, dissolved in suitable ophthalmically acceptable carriers have been demonstrated to effectively provide tear stimulation in the tests below described.

Suitable ophthalmically acceptable carriers are generally known and of course must be non-eye-irritating, non-toxic, and allow for safe, easy eye administration topically. Generally for this invention, aqueous-base systems wherein the carrier includes a buffer system to provide eye safe pH, a viscolyzer to provide suitable viscosity for eye comfort, an antibacterial agent, and a chemical preservative are adequate. The ophthalmically acceptable buffer should provide a composition having a pH within the range of about 5.5 to about 7.8, preferably from about 6.8 to about 7.4. Suitable ophthalmically acceptable buffers can be selected from the water soluble salt forms of citrate, borate, phosphate, carbonate, and acetate.

The viscolyzer suitable for use in this invention should provide the composition with a viscosity within the range of from about 4 centipoises to about 100 centipoises, preferably from about 5 centipoises to about 35 centipoises. Suitable viscolyzers can be selected from the group consisting of hydroxyethylcellulose, hydroxypropyl methylcellulose, methylcellulose and a polyacrylamide sold under the trade name GELAMIDE 250 by American Cyanamide.

In addition, the ophthalmic composition ideally will include antibacterials to provide safety and efficacy for storage stability. The amount of antibacterial can be within the range of from about 0.005% to about 0.2% by weight/volume of the composition. A suitable antibacterial would include, for example, from about 0.005% to about 0.2% by weight/volume of benzalkonium chloride, from about 0.25% to about 0.5% of chlorobutanol, about 0.1% of thimerosal, about 0.05% methylparaben, about 0.01% propylparaben, and sodium chloride in an amount sufficient to make an isotonic solution.

Finally, chemical preservatives may also be used, for example sodium thiosulfate at about a 0.3% level and ethylenediaminetetraacetic acid at about 0.05%. It goes without saying that the precise ophthalmic carrier must be selected to provide pharmaceutical elegance, to provide eye comfort and to allow for effective topical administration. Formulation of such is well within the skill of the ordinary artisan who prepares ophthalmic carrier compositions.

While the ophthalmic compositions of the present invention have been developed primarily to provide a method of topically administering to the eye a composition which treats dry eye syndrome by stimulating the eye's own tear production, it is also contemplated that the compositions of this invention may also be useful in combination with tear substitutes as well.

The following examples are offered to further illustrate but not limit the invention. The first series of examples shows preparation of compounds falling within the scope of the general formula for the active compounds of this invention, and the second series of examples, together with the drawing, illustrates application of these ophthalmically active compounds to the eye of rabbits to stimulate effective tear production. The rabbit eye is known to active investigators in the ophthalmic arts to closely parallel, and predict, and correlate well with human eye activity.

EXAMPLE 1

Preparation of N-cyclohexyl-N-methylbenzylamine

The compound N-cyclohexyl-N-methylbenzylamine was synthesized by treatment of N-methylcyclohexylamine (1) [1.98 ml, 1.70 g, 0.015 moles] with benzyl bromide (2) [1.78 ml, 2.56 g, 0.015 moles] in the presence of potassium carbonate [2.28 g, 1.1 equivalents] in 4-methyl-2-pentanone (50 ml). The reaction mixture was heated under reflux overnight. After filtering the insoluble potassium salts, the filtrate was concentrated to dryness. The solid was dissolved in boiling 4-methyl-2-pentanone, treated with activated carbon, followed by hot filtration after which the purified compound precipitated upon cooling. It was collected by vacuum filtration. m.p. 173.5°–174.5° C. Proton NMR (CDCl$_3$) reported downfield from TMS: 1.11–1.92 ppm multiplet 10 H cyclic alkyl ring, 2.65 ppm singlet 3 H N-methyl, 3.01–3.11 ppm multiplet 1 H tertiary proton, 4.19 ppm singlet 2 H benzylic —CH$_2$—, 7.44–7.80 ppm 5 H aromatic; C-13 nmr 131.12, 130.19, 129.08, 128.40, 63.11, 55.12, 35.23, 26.37, 25.06, 24.33. EI Mass Spec. M/e- (int) M+203 (28.4), M++1 204 (4.7), M++2 205 (0.2), 160 (70.7), 146 (10.6), 91 (100), 92 (7.1), 85 (5.6), 82 (5.2), 70 (17.6), 65 (24.7), 57 (5.7), 56 (5.3), 55 (15.0), 43 (3.6), 42 (32.3), 41 (20.1).

EXAMPLE 2

N-cyclohexyl-N-methyl-2-phenylethylamine

The preparation of N-cyclohexyl-N-methyl-2-phenylethylamine was accomplished in the following manner. This was prepared by treating a suspension of N-methylcyclohexylamine (1.98 ml, 0.015 moles, 1.70 g) and potassium carbonate (4.15 g, 0.03 moles, 2 eq.) in 4-methyl-2-pentanone (50 ml) with phenethylbromide (2.05 ml, 0.015 moles, 2.78 g). The reaction was heated under reflux 16 hours. The insoluble material was removed by a hot gravity filtration and the filtrate was concentrated in vacuo on the rotary evaporator. The resulting oil was flash chromatographed on davisil 633 using 20% ethyl acetate/hexane as the eluent. The appropriate fractions were pooled and concentrated. The oil was dissolved in ether and treated with HCl gas. The resulting precipitate was collected by vacuum filtration and recrystallized from absolute ethanol. m.p. 187°–188° C. EI Mass Spec. M+217(0.9), 126(92.2), 113(4.5), 112(1.2), 105(6.9), 91(32.2), 83(9.8), 77(11.6), 70(66.0), 65(15.9), 57(26.0), 55(39.8), 53(8.6), 45(2.8), 44(100), 43(8.2), 42(42.2), 41(34.9).

EXAMPLE 3

Preparation of N-isopropyl-N-methylbenzylamine

A flask containing N-methylbenzylamine (3.87 ml, 3.63 g, 0.03 moles), potassium carbonate (8.29 g, 0.06 moles) and 4-methyl-2-pentanone (100 ml) was treated with isopropyl bromide (2.69 ml, 0.03 moles) then heated under reflux for 18 hours. The reaction was checked by thin layer chromatography (tlc) to ensure the starting materials had been consumed. The reaction mixture was gravity filtered hot to remove the potassium salts and the filtrate was concentrated to an oil under reduced pressure on the rotovap. The oil was purified by flash chromatography (davisil 633, 20% ethyl acetate/hexane). The appropriate fractions were pooled and concentrated to an oil which was dissolved in anhydrous diethyl ether. The ether solution was treated with gaseous HCl. The ether was removed under reduced pressure. The residue was dissolved in absolute ethanol, treated with activated carbon, filtered, and cooled. The liquid was concentrated with acetone to remove traces of water. The solid was collected by vacuum filtration. m.p. 127.5°–128.5° C. Proton NMR (CDCl3 +TMS) 1.36 doublet J=6.66 Hz 3 H ipr methyl, 1.51 doublet J=6.66 Hz 3 H ipr methyl, 1.88 ppm NH+, 2.62 doublet J=5.04 Hz 3 H N-Methyl, 3.47 septette 1 H tertiary, 4.15 doublet J=6.05 Hz 2 H benzylic CH$_2$—, 7.28–7.42 5 H aromatic; C-13 (DMSO) ref:39.5, 131.16(11.88), 130.53(8.72), 129.12(5.74), 128.56 (10.92), 55.99(2.06), 55.11(7.14), 39.51(1.48), 34.36(6.93), 1845(3.11), 16.89(6.18), 15 19(5.20). EI Mass spec. M/e−(int) M+163(6.3), 148(40.7), 120(1.2), 92(8.0), 91(100), 90(1.5), 89(3.1), 78(2.2), 77(4.1), 65(18.8), 57(1.6), 56(8.1), 51(3.5), 44(6.0), 43(3.5) 42(11.8), 41(5.2).

EXAMPLE 4

N-methyl, N-cyclohexyl, N-methylbenzylammonium Iodide

A purified sample of the sample prepared in Example 1 as the free base (1.0 g, 4.9 mmoles) was dissolved in 10 g of absolute ethanol. Methyl iodide (0.82 ml, 1.86 g, 13.2 mmoles) was added to the reaction mixture via pressure equalizing addition funnel. When the addition was complete, the reaction was heated under reflux for 30 minutes then removed from the heat and transferred to a beaker to cool. A fluffy yellow solid precipitated out upon addition of anhydrous diethyl ether which was collected by vacuum filtration. The solid was washed with additional ether (2×25 ml) and air dried. m.p. 198.5°–200° C. Proton NMR (CDCl$_3$+TMS) 1.333–2.36 multiplet 10 alkyl protons. 3.12 ppm singlet 6 H N-dimethyl, 3.80 multiplet 1 H tertiary proton, 4.87 ppm singlet benzylic CH$_2$- 2 H, 7.42–7.76 5 H aromatic; Carbon-13 (ref: CDCl$_3$77.0 ppm) 132.21(9.7), 129.51(3.68), 127.97(10.0), 126.19(6.2), 72.33(3.47), 63.56(2.07), 46.53(2.82), 25.95(6.2), 24.09(5.8), 23.50(2.7).

EXAMPLES OF TEAR STIMULANT ACTIVITY

Two methods of evaluating increased tear production in the normal rabbit eye have been developed and used. One method involves the use of Schirmer test strips following instillation of a test product. Another method involves the use of a Periotron ®, an instrument originally designed to measure the amount of fluid on the gum surface of the mouth but adaptable to the surface of the eye. With these two methods, one can test many commercial tear substitute products. None showed an increase in the tear film. However, the tear stimulant, bromhexine (0.2 and 0.5%, 100 μL instillation), did not show a statistical increase in the fluid of the tear film in the normal rabbit eye at 30 minutes and 60 minutes after instillation from measurements made with the Periotron. This was used for comparision purposes (see the Drawing). In an earlier study, identical to the one shown in the drawing but measured at 15 and 60 minutes, bromhexine showed statistical significance at 60 minutes compared to baseline measurements.

In the drawing, test results are shown for bromhexine for comparative purposes and the compounds prepared in each of the Examples 1–4 as designated in the Drawing. The preferred compound of this invention, N- cyclohexyl-N-methyl2-phenylethylamine, showed greater potency than the compound produced in Example 1 on a weight basis, and showed greater potency than bromhexine in the normal rabbit eye at 0.2% w/v. The compounds of Examples 3 and 4 show less activity than the preferred compound of Example 2. Clearly the preferred compound of Example 2 showed a statistically significant increase in tear production (see Drawing) over bromhexine.

In conducting these evaluation tests, measurements following topical instillation were made up to one hour. Whenever rabbits were tested on two consecutive days, base line measurements were higher in both eyes. These measurements would decline to previous base line measurements if the rabbits were not used for testing for three or more days.

The test protocol for the measurements shown in the Drawing included the following for use of the Periotron. Small filter strips were placed at the corneal scleral junction for ten seconds. They were then put into the Periotron well which measures how much fluid soaked into the filter strip. These were graded on a scale of from 0 to 100 to calibrate the instrument readings. The standard weight of the dry strip was taken, and water was added to get weight measurements which correlated to a known water content. The active compounds, prepared as earlier described, were dropped into the eye in an isotonic aqueous solution having a small amount of hydrochloric acid present to provide a pH of 4.5. The active drug readily dissolved. In each instance the active drug was used at 0.2% w/v. Prior to administering the dose to the eye, a zero instrument reading was taken to determine the amount of fluid in the rabbit eye without any drug. This is shown in the Drawing as pretest (t=0). This was measured at the limbus in the eye. Thereafter, 100 microliters of the active in two drops was placed in the eye of the rabbit and readings were taken at ½ hour and 1 hour. The instrument readings are recorded on the bar graph illustrated in the Drawing. It can be seen that in each instance, there was initial tear stimulus, as measured at 30 minutes, and as well for the compounds prepared in Examples 1, 2 and 4 at 60 minutes. The compound of Example 3 showed an initial stimulation at 30 minutes, but a decrease at 60 minutes in the tests reported.

The test results here shown, as well as others completed and still in progress, show the compounds of the present invention to be ophthalmically active for tear stimulation when topically applied.

What is claimed is:

1. A method of stimulating lacrimal secretion, comprising:
    topically applying to the eye to stimulate the eye itself to produce more tears from about 0.1% to about 5% on a weight volume basis of a topical ophthalmic preparation of a compound of the formula:

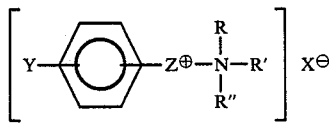

wherein Y is selected from the group consisting of hydrogen, hydroxy, amino, $C_1$ to $C_5$ alkyl, $C_1$ to $C_5$ hydroxyalkoxy and $C_1$ to $C_5$ alkoxy; Z is selected from the group consisting of $C_1$ to $C_6$ alkylene, $C_1$ to $C_6$ oxyalkylene, and $C_1$ to $C_6$ aminoaklylene; R is selected from the group consisting of $C_1$ to $C_6$ alkyl and $C_3$ to $C_7$ cycloalkyl; R' is selected from the group consisting of hydrogen, $C_1$ to $C_6$ alkyl and $C_3$ to $C_7$ cycloalkyl; R'' is selected from the group of hydrogen and $C_1$ to $C_6$ alkyl; and X is a pharmaceutically acceptable counteranion.

2. The method of claim 1 wherein the amount of said compound is from about 0.2% to about 0.6% on a weight/volume basis of a topical ophthalmic preparation.

3. The method of claim 1 wherein the compound applied to the eye s a biologically acceptable salt form of N-cyclohexyl-N-methyl-2-phenylethylamine.

4. An ophthalmically effective tear stimulant composition, comprising:
    from about 0.1% to about 5% on a weight volume basis of said composition of a compound of the formula:

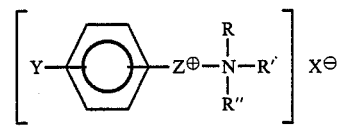

wherein Y is selected from the group consisting of hydrogen, hydroxy, amino, $C_1$ to $C_5$ alkyl, $C_1$ to $C_5$ hydroxyalkoxy and $C_1$ to $C_5$ alkoxy; Z is selected from the group consisting of $C_1$ to $C_6$ alkylene, $C_1$ to $C_6$ oxyalkylene, and $C_1$ to $C_6$ aminoalkylene; R is selected from the group consisting of $C_1$ to $C_6$ alkyl and $C_3$ to $C_7$ cycloalkyl; R' is selected from the group consisting of hydrogen, $C_1$ to $C_6$ alkyl and $C_3$ to $C_7$ cycloalkyl; R'' is selected from the group of hydrogen and $C_1$ to $C_6$ alkyl; and X is a pharmaceutically acceptable counteranion; and
    an ophthalmically acceptable carrier for said compound.

5. The composition of claim 4 wherein the carrier includes an ophthalmically acceptable buffer to provide a composition having a pH within the range of about 5.5 to about 7.8.

6. The composition of claim 4 wherein the pH is within the range of from about 6.8 to about 7.4.

7. The composition of claim 5 wherein the ophthalmically acceptable buffer is selected from the group of water soluble salt forms of citrate, borate, phosphate, carbonate and acetate.

8. The composition of claim 4 wherein the carrier includes an ophthalmically acceptable viscolyzer for eye comfort and a composition viscosity within the range of about 4 centipoises to about 100 centipoises.

9. The composition of claim 8 wherein the viscolyzer is selected from the group consisting of hydroxyethylcellulose, hydroxypropyl methylcellulose, methylcellulose and polyacrylamide.

10. The composition of claim 4 wherein the carrier includes an antibacterial agent.

11. The composition of claim 4 wherein the carrier includes a chemical preservative.

12. The composition of claim 4 wherein the ophthalmic carrier includes a buffer, a viscolyzer, an antibacterial, and a chemical preservative.

* * * * *